June 21, 1960 G. MERRILL Plant Pat. 1,954
PEACH TREE
Filed May 11, 1959
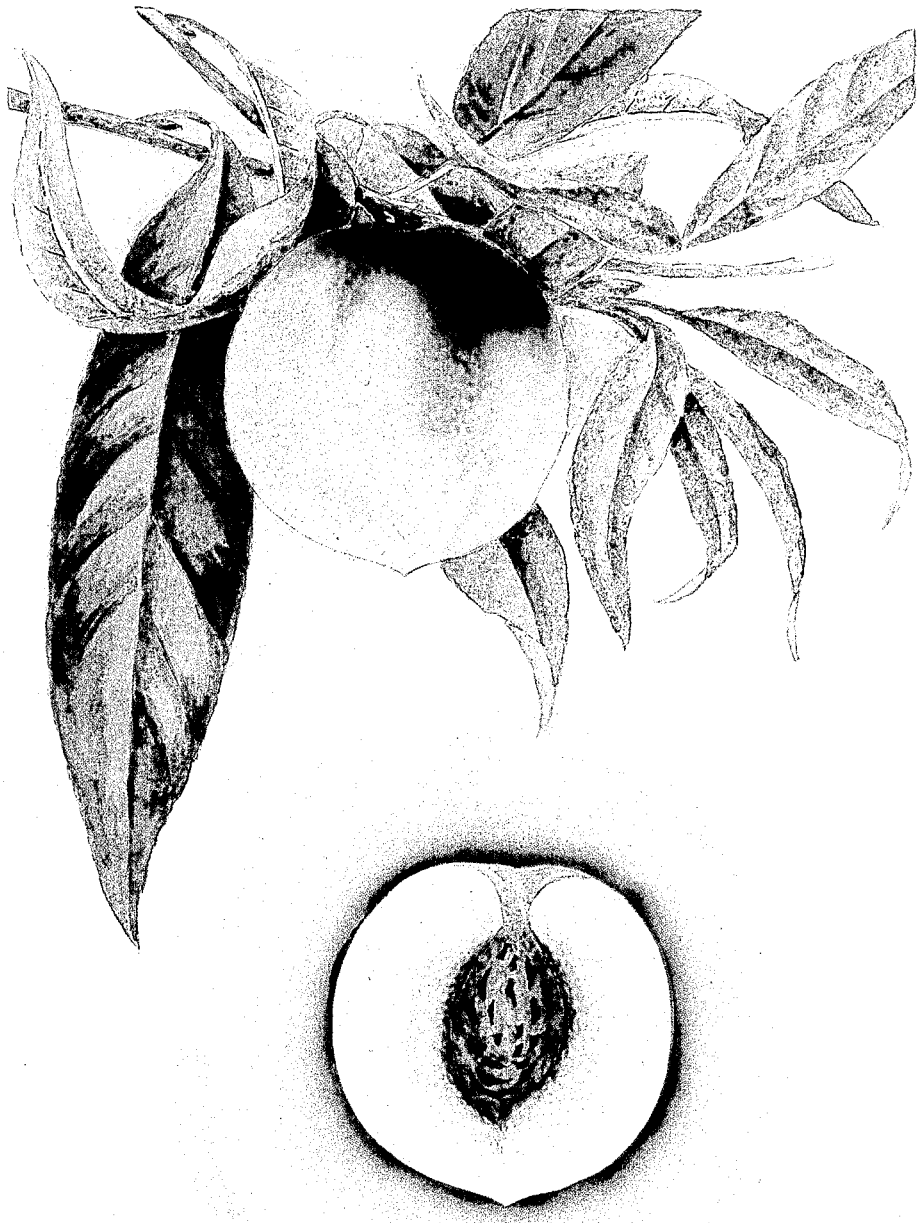
WITNESS
Addison E. Avery
INVENTOR
GRANT MERRILL
ATTORNEYS
HUEBNER & WORREL
BY Richard M. Worrel United States Patent Office Plant Pat. 1,954
Patented June 21, 1960

1,954

PEACH TREE

Grant Merrill, P.O. Box 392, Red Bluff, Calif.

Filed May 11, 1959, Ser. No. 812,569

1 Claim. (Cl. 47—62)

The present invention relates to a peach tree and more particularly to a new and distinct variety thereof broadly characterized by bearing highly colored, yellow firm fleshed, freestone peaches which ripen at approximately the same time as the Rio Oso Gem variety (Plant Patent No. 84).

Because of rich soil and favorable climatic environment prevailing in most of the commercial peach farming areas of California, the peach trees tend to produce rank growth and dense shade resulting in serious impairment of the coloring of the fruit. Inasmuch as most fruits rely on eye appeal for their sales, color impairment is highly undesirable. A primary object of the plant breeding procedures which have resulted in the development of this new peach variety has been to achieve a highly colored red peach which maintains its color even under conditions of rank growth and dense shade.

Another object has been to provide a new peach variety which produces fruit of satisfactory size without excessive pruning or thinning.

A collateral object has been to produce a new peach variety characterized by moderate but consistent fruit set, minimizing pruning and thinning requirements without being subject to irregular production.

Another object has been to provide a peach tree of the character described which is vigorous and healthy but of medium size so as to be susceptible to picking without excessively tall ladders and yet be of sufficient size to produce satisfactory yields when planted the usual commercial distances.

Further objects and advantages will become apparent in the subsequent description in the specificiation.

In the drawing:

Fig. 1 is a water color painting of a characteristic fruit bearing twig of the subject peach tree having leaves and a mature peach thereon.

Fig. 2 is a water color painting showing a characteristic fruit of the subject peach tree divided on its suture plane to reveal flesh coloration and showing a pit in place therein.

The most distinctive characteristic of the instant variety of peach tree is that its fruit has more red on its skin surface, and is firmer fleshed than other freestone peaches ripening at the same time.

The instant variety most nearly resembles Rio Oso Gem (Plant Patent No. 84), but is an improvement thereon in that it has a more vigorous tree, the fruit has a less pronounced suture ridge, has more red skin color, holds its firmness longer after it develops full color.

This new variety of peach was produced by me on my breeding farm near Red Bluff, Tehama County, California. J. H. Hale (unpatented) was crossed with an open pollinated seedling from a tree which was a seedling resulting from a cross of July Elberta (Plant Patent No. 15) with Maxine (unpatented). Expressed in formula form it would be: J. H. Hale × ((July Elberta × Maxine) × open).

The present variety was asexually propagated by grafting onto a tree of Merrill June (Plant Patent No. 869) growing on my farm at Lamont, Kern County, California. When this tree came into bearing the tree, fruit and other characteristics of this peach tree proved to be identical with the original peach tree.

Referring more specifically to the pomological characteristics of this new and distinct variety of peach tree, the following have been observed under the ecological conditions prevailing at my farm near Red Bluff, Tehama County, California, and is an outline description thereof; all major color plate identifications being by reference to Maerz and Paul Dictionary of Color.

*Tree*

Shape: Medium size, vigorous, neither upright nor spreading but medium in shape, productive, regular bearer.

Trunk: Medium stocky, medium shaggy, brownish grey in color.

Branches: Older branches, greyish and shaggy, younger branches, brown to reddish brown and more smooth. Lenticels—medium in quantity, medium in size.

Leaves (selected from midportion of vigorous unbranched terminal shoot 18″ to 24″ long):

*Length.*—6½″ to 7½″. Average 6⅞″.

*Width.*—1 5/16″ to 1 9/16″. Average 1½″.

*Form.*—Medium size, lanceolate, tip acuminate, medium thick.

*Color.*—Yellowish Green (22–L–7 plus yellow). Underside (22–K–5). Heavy underrib (10–J–1)

*Class (Meader and Blake: Proceedings: Am. Soc. Hor. Sc., vol 37, page 206.)*—2 to 3. Width length ratio—22. Apex angle (1″ from tip)—23°–30°; average 24½°. Base angle (½″ from petiole)—75°–84°; average 80°.

*Margin.*—Crenate.

*Petiole.*—Medium short, medium slender.

*Stipules.*—At base of leaf, falling off early.

*Glands.*—2 to 4, average 3, opposite and alternate, medium size, reniform, green to yellowish green, on petiole and base of leaf.

Flower buds: Medium size, medium length, plump, free, pubescent.

Flowers: Bloom moderately early, about with Elberta (unpatented); small size; pink; moderately abundant.

*Fruit*

Maturity when described: Eating to firm ripe.

Size: Fairly uniform, medium to large. Axial diameter—2½″ to 3″; average 2¾″. Transverse in suture plane—2⅝″ to 3″; average 2 13/16″. At right angles to suture plane—2½″ to 3″; average 2¾″.

Form: Globose, tip mucronate to cuspidate.

*Suture.*—Usually a definite line, but not conspicuous in most fruits, in some fruits conspicuous.

*Ventral surface.*—Rounded, slightly lipped on one side.

*Cavity.*—Rounded to slightly elongated in suture plane with suture showing on both sides. Depth ½″ to ⅝″, average 9/16″. Breadth—½″ to 11/16″, average 9/16″. Markings—yellow undercolor to full red blush.

*Base.*—Rounded.

*Apex.*—Mucronate to cupsidate, pistil point, apical.

*Stem.*—Medium short, length ⅜″; diameter ⅛″; adheres to stone on a few.

*Skin.*—Medium thick, medium tender, tenacious to flesh; tendency to crack—none; color—yellow under color (10–K–7) to (3–J–10) with extensive blush, brownish red (4–K–10) to dark red (7–L–6); spots and stripes on some; down—scant, short, does not roll up when rubbed.

Flesh:

*Color.*—Most of the flesh yellowish (9–K–6) to (9–L–7) with a whitish-yellow near stone (9–B–5) and red at stone (5–K–6).

*Surface of pit cavity.*—Red to pink, with red fibers.

*Amygadalin.*—Scant.

*Juice.*—Moderate.

*Texture.*—Firm, fine, meaty.

*Fibers.*—Few, fine.

*Ripens.*—Evenly.

*Flavor.*—Mild, delicate.

*Aroma.*—Distinct.

*Eating quality.*—Good.

Stone: Free with a few short fibers remaining along the ridge on some stones; adherence to flesh, none.

*Size.*—Medium to small. Length—1¼″ to 1½″; average 1 11/32. Breadth—¾″ to 1⅛″; average 1″. Thickness—⅝″ to 15/16″; average ¾″.

*Form.*—Obovate, apex cuspidate.

*Base.*—Some straight, mostly oblique.

*Hilum.*—Oval.

*Sides.*—Usually slightly unequal but varying from equal to pronounced inequality.

*Surface.*—Irregularly furrowed near base and near apex, pitted throughout central portion. Ventral edge—many small, narrow grooves, deep groove on either side. Dorsal edge—irregularly furrowed, usually discontinuous near tip.

*Color.*—(8–L–10).

*Tendency to split.*—Slight.

Use: Market, dessert, long distance shipping.

Keeping quality: Good.

It has further been observed that the fruit is relatively free of split pits and growing cracks, hangs on the tree well in spite of windy conditions, resists skin tearing during picking, packing and other handling, is subject to a minimum of skin cutting by the stems because of their relatively short length, possesses a high ascorbic acid (vitamin C) content demonstrated by color retention of the flesh when exposed to the air.

Although the new variety of peach tree possesses the described characteristics under the growing conditions prevailing throughout most of the commercial peach producing areas of California, having been first observed near Red Bluff, Tehama County, California at the northern end of the Sacramento Valley and later confirmed by observation of the same variety near the southern end of the San Joaquin Valley of California approximately four hundred miles farther south, it is to be understood that variations of the usual magnitude in characteristics incident to growing conditions, fertilization, pruning, thinning and pest control are to be expected.

Having thus described my new peach tree, what is claimed as new and desired to be secured by Letters Patent is:

A new and distinct variety of peach tree, substantially as illustrated and described, characterized by highly colored firm yellow fleshed freestone peaches ripening with the variety Rio Oso Gem (Plant Patent No. 84) but distinguished from Rio Oso Gem (Plant Patent No. 84) and being an improvement thereon by having a more vigorous tree, generally less pronounced suture, redder skin color, and a tendency of the fruit to hold its firmness longer when fully colored.

No references cited.